(12) United States Patent
Amplatz et al.

(10) Patent No.: US 8,163,004 B2
(45) Date of Patent: Apr. 24, 2012

(54) STENT GRAFT FOR REINFORCEMENT OF VASCULAR ABNORMALITIES AND ASSOCIATED METHOD

(75) Inventors: Kurt Amplatz, St. Paul, MN (US); Robert Laine, Plymouth, MN (US)

(73) Assignee: AGA Medical Corporation, Plymouth, MN (US)

( * ) Notice: Subject to any disclaimer, the term of this patent is extended or adjusted under 35 U.S.C. 154(b) by 392 days.

(21) Appl. No.: 12/032,938

(22) Filed: Feb. 18, 2008

(65) Prior Publication Data

US 2009/0210047 A1 Aug. 20, 2009

(51) Int. Cl.
*A61F 2/06* (2006.01)
(52) U.S. Cl. ...................... 623/1.18; 623/1.13
(58) Field of Classification Search .............. 623/1.13, 623/1.15, 1.18, 1.2, 1.53; 606/200
See application file for complete search history.

(56) References Cited

U.S. PATENT DOCUMENTS

| | | | |
|---|---|---|---|
| 4,441,215 A | 4/1984 | Kaster |
| 4,655,771 A | 4/1987 | Wallsten |
| 4,728,328 A | 3/1988 | Hughes et al. |
| 5,064,435 A | 11/1991 | Porter |
| 5,522,881 A | 6/1996 | Lentz |
| 5,562,725 A | 10/1996 | Schmitt et al. |
| 5,628,788 A | 5/1997 | Pinchuk |
| 5,709,713 A | 1/1998 | Evans et al. |
| 5,755,772 A | 5/1998 | Evans et al. |
| 5,758,562 A | 6/1998 | Thompson |
| 5,800,508 A | 9/1998 | Goicoechea et al. |
| 5,916,264 A | 6/1999 | Von Oepen et al. |
| 5,957,974 A | 9/1999 | Thompson et al. |
| 6,110,198 A | 8/2000 | Fogarty et al. |
| 6,123,715 A | 9/2000 | Amplatz |
| 6,299,636 B1 | 10/2001 | Schmitt et al. |
| 6,468,301 B1 | 10/2002 | Amplatz et al. |
| 6,488,705 B2 | 12/2002 | Schmitt et al. |
| 6,500,203 B1 | 12/2002 | Thompson et al. |
| 6,709,451 B1 | 3/2004 | Noble et al. |
| 6,709,455 B1 | 3/2004 | Chouinard |
| 6,860,900 B2 | 3/2005 | Clerc et al. |
| 6,866,679 B2 | 3/2005 | Kusleika |
| 6,932,837 B2 | 8/2005 | Amplatz et al. |
| 6,974,586 B2 | 12/2005 | Greenhalgh et al. |
| 7,052,513 B2 | 5/2006 | Thompson |
| 7,147,656 B2 | 12/2006 | Andreas et al. |
| 2002/0068967 A1 | 6/2002 | Drasler et al. |
| 2004/0024416 A1 | 2/2004 | Yodfat et al. |
| 2005/0209678 A1 | 9/2005 | Henkes et al. |
| 2006/0106455 A1* | 5/2006 | Furst et al. ................ 623/1.31 |
| 2006/0206201 A1 | 9/2006 | Garcia et al. |

(Continued)

FOREIGN PATENT DOCUMENTS

WO WO 2007/087005 A2 8/2007

*Primary Examiner* — Thomas J Sweet
*Assistant Examiner* — Seema Swaminathan
(74) *Attorney, Agent, or Firm* — Alston & Bird LLP (57) ABSTRACT

A stent graft for reinforcement of a vascular abnormalities and an associated method are provided. According to one embodiment, the stent graft includes a flexible tubular structure comprising a proximal end and a distal end and having an expanded heat set configuration. The tubular structure is configured to be constrained to a smaller diameter than the expanded heat set configuration, and the tubular structure is heat set such that at least a portion of the proximal and/or distal ends is configured to fold over on itself when unconstrained.

31 Claims, 3 Drawing Sheets

U.S. PATENT DOCUMENTS

| | | |
|---|---|---|
| 2006/0212055 A1* | 9/2006 | Karabey et al. ............... 606/158 |
| 2006/0253184 A1 | 11/2006 | Amplatz |
| 2007/0168018 A1 | 7/2007 | Amplatz et al. |
| 2007/0168019 A1 | 7/2007 | Amplatz et al. |
| 2009/0222076 A1* | 9/2009 | Figulla et al. .................. 623/1.2 |
| 2010/0023046 A1 | 1/2010 | Heidner et al. |
| 2010/0023048 A1 | 1/2010 | Mach |

* cited by examiner

STENT GRAFT FOR REINFORCEMENT OF VASCULAR ABNORMALITIES AND ASSOCIATED METHOD

BACKGROUND OF THE INVENTION

1) Field of the Invention

The present invention relates to an endovascular prosthesis and, in particular, to a stent graft for treating vascular abnormalities, such as an aneurysm.

2) Description of Related Art

An aortic aneurysm is a weak area in the aorta, the main blood vessel that carries blood from the heart to the rest of the body. A common aneurysm is the abdominal aortic aneurysm ("AAA"), which may be caused by arteriosclerosis. As blood flows through the aorta, the weak vessel wall thins over time and expands like a balloon and can eventually burst if the vessel wall gets too thin. Most commonly, aortic aneurysms occur in the portion of the vessel below the renal artery origins. The aneurysm may be located in the vessels supplying the hips and pelvis, including the iliac arteries.

Once an aneurysm reaches about 5 cm in diameter, it is usually considered necessary to treat to prevent rupture. Below 5 cm, the risk of the aneurysm rupturing is lower than the risk of conventional heart surgery in patients with normal surgical risks. The goal of therapy for aneurysms is to prevent the aorta from rupturing. Once an AAA has ruptured, the chances of survival are low, with 80-90 percent of all ruptured aneurysms resulting in death. These deaths can be avoided if the aneurysm is detected and treated before it ruptures and ideally treated at an early stage (i.e., when the aneurysm is smaller than about 5 cm) with a lower risk procedure.

Aneurysms may be treated with surgery. The surgical procedure for treating AAA involves replacing the affected portion of the aorta with a synthetic graft, usually comprising a tube made out of an elastic material with properties very similar to that of a normal, healthy aorta. However, surgical treatment is complex and may pose additional risks to the patient, especially the elderly.

More recently, instead of performing surgery to repair an aneurysm, vascular surgeons have installed an endovascular stent graft delivered to the site of the aneurysm using elongated catheters. An endovascular stent graft is a tube composed of blood impervious fabric supported by a metal mesh called a stent. It can be used for a variety of conditions involving the blood vessels, but most commonly is used to reinforce a weak spot in an artery called an aneurysm. The term "stent" refers to a device that is primarily metallic, such as a balloon or self expanding stent, and maintains patency of a lumen. Typically, the surgeon will make a small incision in the patient's groin area and then insert into the vasculature a delivery catheter containing a collapsed, self-expanding or balloon-expandable stent graft to a location bridging the aneurysm, at which point the stent graft is delivered out from the distal end of the delivery catheter and expanded to approximately the normal diameter of the aorta at that location. Over time, the stent graft becomes endothelialized and the space between the outer wall of the stent graft and the aneurysm ultimately fills with clotted blood, which prevents the aneurysm from growing further since the stent graft bypasses (excludes) the aneurysm and prohibits systematic pressure and flow on the weakened segment of the lumen.

Depending on where the aneurysm is in relation to other branch vessels, different design variations may be needed. For example, in treating AAA, the stent graft should be placed so as not to exclude blood flow through the renal arteries which branch off from the abdominal aorta. Moreover, the stent graft should be anchored within the lumen to reduce the incidence of migration, such as by promoting endothelialization or fixation with the lumen. Endoleaks may occur as a result of blood flowing around the stent, which may result in further weakening of the site of the aneurysm.

Furthermore, the size of the delivery catheter may affect the ability of the surgeon to manipulate the catheter within the lumen, often reduced in size due to arteriosclerosis, and may result in trauma to the vascular tissue. Thus, the smaller the delivery catheter, the less trauma to the tissue should occur, and the stent should be more easily and accurately positioned within the lumen. Smaller delivery catheters would also allow a physician access to smaller vessels, so as to more proactively treat aneurysms. Also, smaller aneurysms are typically easier to treat than larger aneurysms (e.g., aneurysms of at least 5 cm in diameter) because smaller aneurysms are more centrally located between the renal arteries and the iliac bifurcation and also because small aneurysms are more symmetrical and usually do not yet include tortuosity nor involve the iliac arteries.

Conventional stent grafts are typically too bulky to be delivered to treat smaller aneurysms. For example, U.S. Pat. No. 5,800,508 to Goicoechea et al., U.S. Pat. No. 5,916,264 to Von Oepen et al., U.S. Pat. No. 6,110,198 to Fogarty et al., and U.S. Pat. No. 6,709,451 to Noble et al. disclose stent grafts for treating various vascular abnormalities. Although these stent grafts may be radially compressed for delivery, the stent grafts are not configured to be significantly constrained and elongated and may, thus, exhibit a bulkiness that prevents such stent grafts from being delivered to treat smaller aneurysms.

Therefore, there is a need for a stent graft that is capable of being deployed within a variety of lumens for treating aneurysms. Moreover, there is a need for a stent graft that may be easily delivered and adequately anchored within the lumen. In addition, there is a need for a stent graft that may be delivered within a lumen that is less traumatic to the vasculature and that may be used to prophylactically treat an aneurysm before becoming large enough to pose a significant health risk to the patient.

BRIEF SUMMARY OF THE INVENTION

Embodiments of the present invention may provide improvements over the prior art by, among other things, providing a stent graft for treating vascular abnormalities, such as an aneurysm. According to one embodiment of the present invention, a stent graft for treating a vascular abnormality in a lumen includes a flexible tubular structure comprising a proximal end and a distal end and having an expanded heat set configuration. The tubular structure is configured to be constrained to a smaller diameter than the expanded heat set configuration, and the tubular structure is heat set such that at least a portion of the proximal and/or distal ends is configured to fold over on itself when unconstrained. For example, the stent graft may be configured to engage the lumen upstream and downstream of an aneurysm.

Various aspects of the stent graft include a tubular structure having a plurality of layers of braided strands. In addition, the layers may include respective tubular structures coaxially disposed in an overlying relationship and that are joined together by a connecting member. One embodiment of the tubular structure includes braided strands of an elastic metallic alloy.

Additional aspects of the stent graft include a tubular structure including an inner surface and an outer surface, wherein the tubular structure is configured to fold back on itself such that at least a portion of the inner surface of the tubular structure at the proximal and/or distal ends is facing outwardly to engage the lumen. The tubular structure may be configured to fold back on itself such that a first portion of the outer surface lies adjacent to a second portion of the outer surface. Moreover, the tubular structure may be configured to fold back on itself about a circumference of the tubular structure. The tubular structure, including large diameter AAA stent grafts, may also be configured to be constrained to a diameter of less than about 15 French for delivery within a catheter. Furthermore, the tubular structure may be configured to fold back on itself without applying a compressive force thereto or employing a weakened fold line. In addition, a ratio of a diameter of the expanded heat set configuration to the smaller second diameter may be within the range of about 3:1 to 7:1.

A further aspect of the present invention provides a method for treating a vascular abnormality in a lumen. The method includes constraining a stent graft to a smaller diameter than an expanded heat set configuration and delivering the stent graft proximate to the vascular abnormality in the lumen. In addition, the method includes deploying the stent graft such that at least a portion of the proximal and/or distal ends is configured to self expand from the constrained smaller diameter and return to its expanded heat set configuration, fold over on itself, and engage the lumen.

Variations of the method include deploying the stent graft such that the stent graft engages the lumen upstream and downstream of an aneurysm. Moreover, the deploying step may include urging the stent graft distally after the distal end initially expands outwardly to engage the lumen. An additional aspect of the method includes deploying the stent graft after the distal end is urged distally such that the distal end folds over on itself. The deploying step may further include deploying the stent graft such that at least a portion of an inner surface of the stent graft at the distal end folds over to face outwardly to engage the lumen. Furthermore, the deploying step may include deploying the stent graft such that at least of the portion of the stent graft folds back on itself about a circumference thereof. The constraining step may include radially compressing the stent graft to a diameter of less than about 15 French, and/or elongating the stent graft to a smaller diameter. In addition, the delivering step may include delivering the stent graft over a guide wire.

An additional embodiment of the present invention provides a stent graft for treating a vascular abnormality in a lumen that includes a tubular structure of an occlusive material (e.g., a plurality of braided strands) comprising a proximal end and a distal end and having an expanded heat set configuration. The tubular structure is configured to be constrained to a smaller diameter than the expanded heat set configuration, and the tubular structure is heat set such that at least a portion of the stent graft is configured to form a fold when unconstrained. For example, the tubular structure may be heat set such that at least a portion of the proximal and/or distal ends is configured to self expand and fold over on itself when unconstrained.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
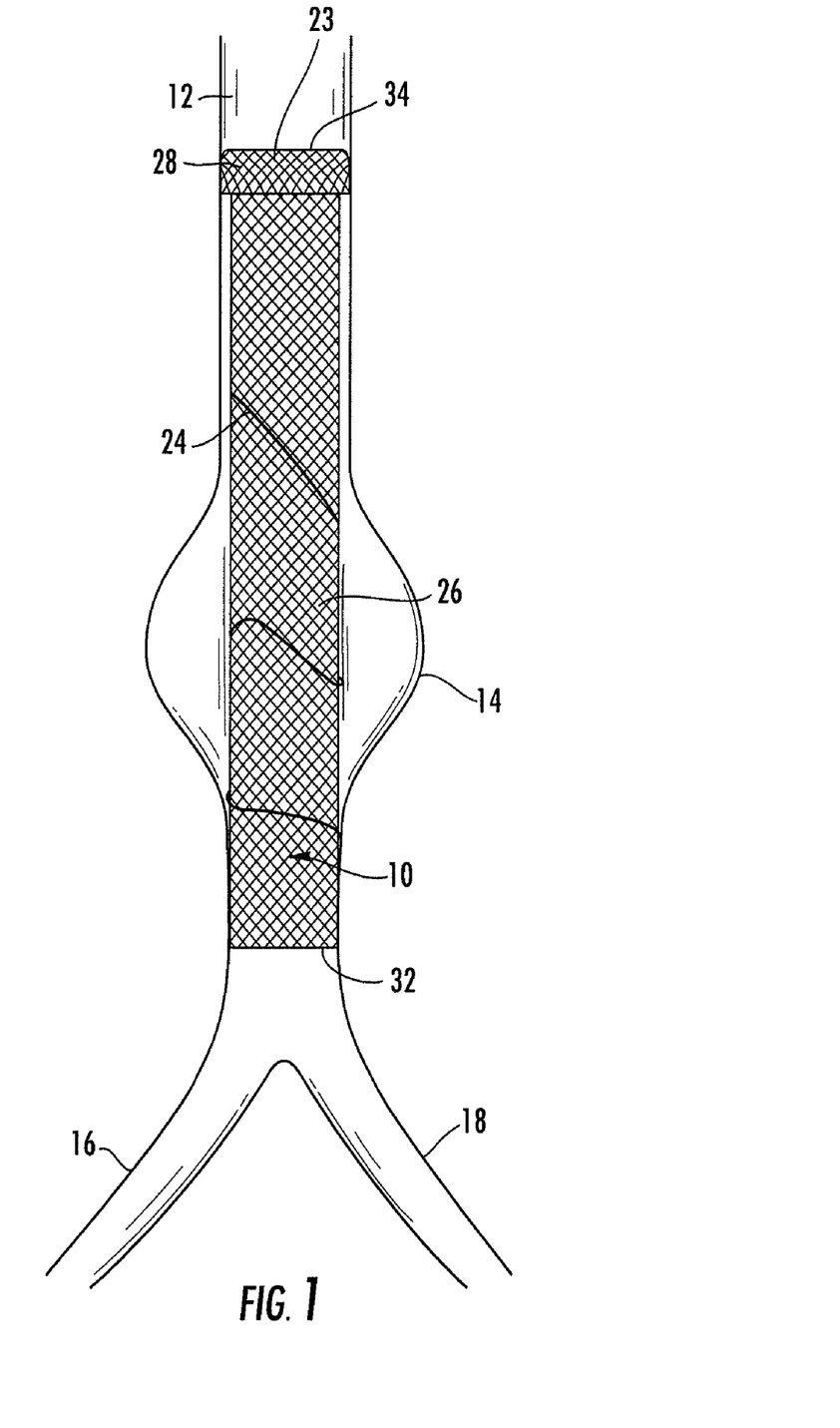
FIG. 1 is a side elevational view of a stent graft positioned within a lumen and bridging an aneurysm according to one embodiment of the present invention.

With reference to FIG. 1, a stent graft 10 is shown positioned within a lumen 12 having a vascular abnormality, such as an aneurysm 14. According to one embodiment, the lumen 12 is the abdominal aorta that branches into the left and right common iliac arteries 16 and 18. As illustrated in FIG. 1, the stent graft 10 is configured to bridge the aneurysm 14 and includes a folded portion 28 that engages the lumen 12. As explained in further detail below, the folded portion 28 is configured to self expand and fold over upon itself to a heat set configuration so as to fixate the stent graft within the lumen and provide additional hoop strength.

The term "vascular abnormality," as used herein is not meant to be limiting, as the stent graft 10 may be configured to bridge or otherwise support a variety of vascular abnormalities. For example, the vascular abnormality could be any abnormality that affects the shape of the native lumen 12, such as an aneurysm, a lesion, a vessel dissection or a tumor. Furthermore, the term "lumen" is also not meant to be limiting, as the vascular abnormality may reside in a variety of locations within the vasculature, such as a vessel, an artery, a vein, a passageway, an organ, a cavity, or the like.

The stent graft 10 may include one or more layers of occlusive material, wherein each layer comprises a tubular structure. The occlusive material may be any material that is configured to impede the flow of blood therethrough so as to facilitate thrombosis. According to one embodiment, FIG. 1 illustrates that an inner tubular member 23 may be coaxially disposed within an outer tubular member 26. The tubular structures 23, 26 comprise a plurality of braided strands, preferably of a shape memory metallic alloy, such as Nitinol. Thus, at least a portion of each of the tubular structures 23, 26 may be configured to self-expand and contact the lumen 12 so as to anchor the stent graft 10 therein. The braid of the tubular structures 23, 26 may be chosen to have a predetermined pick and pitch to define openings or fenestrations so as to vary the impedance of blood flow therethrough. Although the term "strand" is discussed herein, "strand" is not meant to be limiting, as it is understood the braided tubular structure may comprise one or more wires, cords, fibers, filaments, cables, threads, or the like, such that such terms may be used interchangeably.

As used herein, "substantially preclude or impede flow" shall mean, functionally, that blood flow may occur for a short time, e.g., about 5-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the stent graft and if no contrast media flows through the stent graft wall after a predetermined period of time as viewed by fluoroscopy, then the position and occlusion of the stent graft is adequate. Moreover, occlusion of the aneurysm 14 could be assessed using various echo modalities.

As used herein the term "proximal" shall mean closest to the operator (less into the body) and "distal" shall mean furthest from the operator (further into the body). In positioning of the stent graft from a downstream access point, distal is more upstream and proximal is more downstream.

Moreover, the lengths of the tubular structures 23, 26 could also be varied with respect to one another. For example, the inner tubular structure 23 could be longer in length than the outer tubular structure 26 and include openings that are sufficiently large so as to occlude flow parallel to the wall but not to materially impede blood flow through its fenestrated wall, such as proximate to a branching artery. In addition, the tubular structures 23, 26 could comprise a plurality of wire strands and be braided so as to have a pick and pitch to define openings sufficiently small so as to substantially preclude blood flow therethrough, such as proximate to an aneurysm 14. Furthermore, even smaller fenestrations can be provided over at least a portion of the stent graft 10 by having a third, outermost, tubular braided structure coaxially surrounding the outer tubular structure 26. Thus, the stent graft 10 may include any number of layers of tubular structures (i.e., one or more) in order to achieve a desired amount of occlusive material and a desired size of fenestrations in specific portions of the stent graft.

To achieve adequate fixation within the lumen, the diameter of the stent graft 10 is configured to self expand to a diameter that is sized to be larger than, and exert an outward force against, and provide complete circumferential apposition to the diameter of the native lumen 12. For example, the stent graft 10 diameter may be oversized in the range of 10-30%. Moreover, the stent graft 10 may be oversized at the proximal 32 and/or distal 34 ends of the stent graft 10 so as to improve fixation within the lumen 12 upstream and/or downstream of the aneurysm 14.

According to one embodiment, each tubular structure 23 may comprise about 36-144 wire strands ranging in diameter from about 0.001 to 0.012 inches formed of a shape memory alloy, such as Nitinol, that are woven so as to exhibit fenestrations with an area of about 0.00015 to 0.1 sq. in., which are sufficiently small so as to slow the blood flow through the portion of the stent graft 10 wall and to facilitate thrombus formation thereon. Inner and outer braided layers may have pitch rates that are about equal to obtain desirable collapse and expansion characteristics, such as maintaining a uniform overall length. According to one exemplary embodiment, the length of the inner tubular structure 23 is about 10 to 30 cm, and the length of the outer tubular segment 26 is about 8-18 cm, although the tubular structures may be various lengths, as described above. However, it is understood that in alternative embodiments, the tubular structures 23, 26 may be the same length, or the outer tubular structure may be longer than the inner tubular structure. According to one aspect of the present invention, the permeability through the composite wall of the stent graft, composed of multiple layers, is greater than 100 cc/sq. cm/min. at 120 mm Hg. pressure. This porosity is greater than conventional stent grafts and allows blood to temporarily flow easily through the graft wall, but the porosity is low enough to cause blood clotting between the vascular wall and the stent graft, thereby promoting in growth of tissue into the openings of the stent graft from the vascular wall to strengthen the vascular wall to resist any growth in the size of the aneurysm. The stent graft internal wall later becomes covered with endothelial cells as in a natural artery.

The tubular structural layers 23, 26 may be coupled together using various techniques. For example, the tubular structures 23, 26 may be coupled using stitching, such as with platinum radiopaque wire strands. The stitching may be various sizes, such as having a diameter in the range of about 0.001 to 0.006 in. at one or more locations around the circumference the stent graft 10, ideally positioned at a midpoint along the longitudinal axis. Using radiopaque wire strands facilitate visualization and positioning of the stent graft within the lumen 12, as well as allows the multiple braided layers to freely move during collapse and expansion. By holding the layers together at or near the center of the stent graft 10, the relative position of the layers in relation to one another may be substantially fixed, but the proximal 32 and distal 34 ends of the layers may have additional freedom to independently and fully expand.

It is understood that various connecting members other than stitching may be utilized to couple the tubular layers 23, 26 together. For example, one or more radial (helical) stitches 24 may be used to couple the tubular structures 23, 26 substantially along the length of the stent graft, as shown in FIG. 1. The radial stitches 24 could be Nitinol and could be heat set at the same time the graft is heat set. Furthermore, stitching may also be placed at various locations other than the center of the stent graft 10 such as spaced along the length of the stent graft. In addition, other types of connecting members, such as sutures or radiopaque rivets may be used, or the geometry or wire engagement between the layers could be configured to engage one another.

It is also understood that the stent graft may comprise various materials other than Nitinol that have elastic properties, such as spring stainless steel, trade named alloys such as Elgiloy, or Hastalloy, Phynox, MP35N, CoCrMo alloys or a mixture of metal and polymer fibers. Polymer fibers may include monofilaments or multifilament yarns ranging from about 10-400 denier. Individual filaments may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or the tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands and pitch may be altered to achieve the desired properties of the stent graft 10. Furthermore, the proximal 32 and/or distal 34 ends of the tubular members may flare radially outward (e.g., 10-30 degrees) from the longitudinal axis of the stent graft 10 to improve end wire seating and anchoring in the lumen 12.

The stent graft 10 may be various sizes and configurations. For example, the stent graft 10 could include the following dimensions according to various aspects of the present invention:

| OD (mm) | EST'D COLLAPSED OD (inches) | EST'D COLLAPSED LENGTH (mm) |
| --- | --- | --- |
| 6 | 0.065 | 60 |
| 7 | 0.070 | 62 |
| 8 | 0.070 | 66 |
| 9 | 0.080 | 63 |
| 10 | 0.080 | 66 |
| 12 | 0.090 | 77 |
| 14 | 0.090 | 95 |

The outer diameter (OD) corresponds to the unconstrained OD of the stent graft 10, while the collapsed OD and length may correspond to a size for delivery within a catheter, although such sizes may vary depending on the extent that the stent graft is collapsed. According to a further aspect of the stent graft 10, the stent graft may be configured to fit within various sized catheters. For example, a stent graft having an OD of about 17-23 mm may fit within a catheter having an inner diameter (ID) of about 0.150 inches, while a stent graft having an OD of about 24-26 mm may be carried by a catheter having an ID of about 0.163 inches.

For further details regarding the structure, exemplary dimensions, and method of making a stent graft in accordance with additional aspects of the present invention, Applicants hereby incorporate by reference U.S. Patent Appl. Publ. No. 2007/0168018, filed on Jan. 13, 2006, and U.S. Patent Appl. Publ. No. 2007/0168019, filed on Jan. 17, 2007, herein in their entirety.

As briefly mentioned above, the stent graft 10 is heat set such that at least a portion of the stent graft is configured to fold over on itself to define a folded portion 28, as shown in FIG. 1. The folded portion 28 of the stent graft is of slightly larger diameter than the remaining portion of the stent graft 10. Thus, the folded portion 28 may facilitate fixation of the stent graft within the lumen and prevent migration of the stent graft following implantation.

According to one embodiment, the folded portion 28 is located at the distal end 34 of the stent graft 10. Thus, the folded portion 28 may be located upstream of an aneurysm, such as in the abdominal aorta upstream of the left and right common iliac arteries 16 and 18, as shown in FIG. 1. However, it is understood that the stent graft 10 could include one or more folded portions 28, such as at the proximal 32 and distal 34 ends of the stent graft. In addition, the folded portion 28 may extend either inwardly within the lumen of the stent graft 10 or outwardly to overlie the outer surface of the stent graft. For example, the folded portion 28 may be at the proximal end 32 and folded inward due to the likelihood that an outward fold may get caught on the vessel wall before it has a chance to fold over since no portion would be retained within a delivery catheter. Moreover, the distal end 34 of the stent graft 10 may have the wire ends flared slightly outward to help engage the vessel wall to prevent migration. Furthermore, the stent graft 10 could be heat set such that a portion of the stent graft between the proximal 32 and distal 34 ends could fold over on itself, such as a middle portion of the stent graft to increase the hoop strength of the stent graft 10 (e.g., in the region of a tumor or other abnormality that is restricting the lumen 12). The length of the folded portion 28 may vary depending on the amount of additional hoop strength and fixation desired, but is typically within the range of 15-40% of the diameter of the stent graft 10 or 3-25% of the total length of the stent graft.

Figure 2:
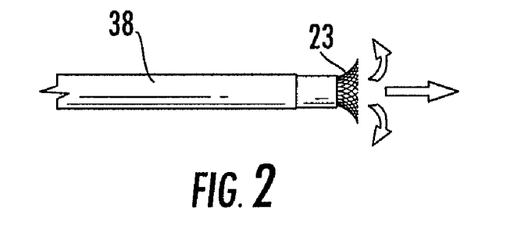
FIGS. 2-6 are side elevational views of a stent graft being deployed from a catheter according to one embodiment of the present invention.
Figure 3:
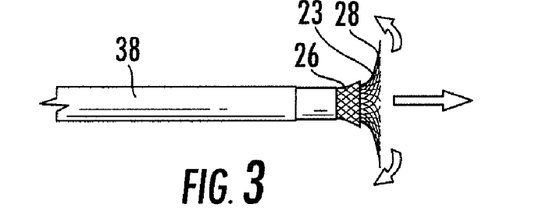
Figure 4:
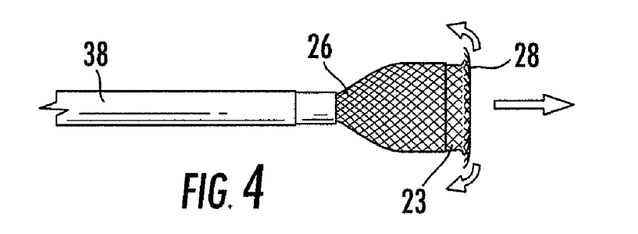
Figure 5:
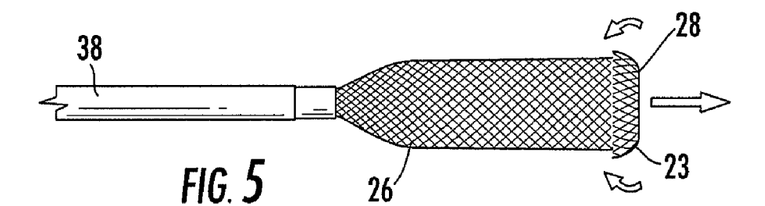
Figure 6:
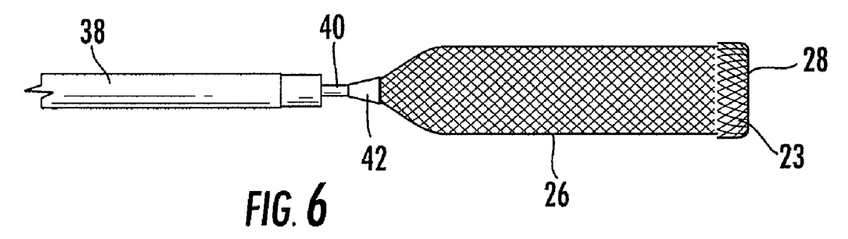

FIGS. 2-6 illustrate the progression of deployment of the stent graft 10 from a delivery catheter 38. As shown in FIG. 2, when the distal end of the tubular structure 23 is deployed from the delivery catheter 38, the tubular structure 23 expands outwardly. Due to the propensity of the stent graft 10 to return to its heat set configuration when released, the distal end 34 continues to fold outwardly and back, as shown in FIGS. 3-5. Thus, the distal end 34 of the tubular structure 23 expands outwardly about its circumference and folds back such that an inner surface of the tubular structure faces outwardly. Typically, the inner tubular structure 23 is of slightly longer length than the outer tubular structure 26, at least at the distal end 34 of the stent graft, as shown in FIGS. 3 and 4. As such, the distal end 34 of the tubular structure 23 may fold over on itself or on itself and a portion of the distal end of the tubular structure 26 depending on the length of the folded portion and the differences in length between the tubular structures 23, 26. When the distal end 34 of the tubular structure 23 is completely released, the folded portion 28 has already returned to its heat set position, as illustrated in FIG. 6. Therefore, a portion of the inner surface of the tubular structure 23 defines the folded portion 28 and is configured to engage the lumen 12 about its circumference. When fully deployed and unconstrained, the folded portion 28 is configured to lie in intimate relationship with the underlying portion of the stent graft 10 and the lumen 12 and may thereby provide additional hoop strength about the distal end 34 of the stent graft and additional fixation within the lumen 12.

Figure 7:
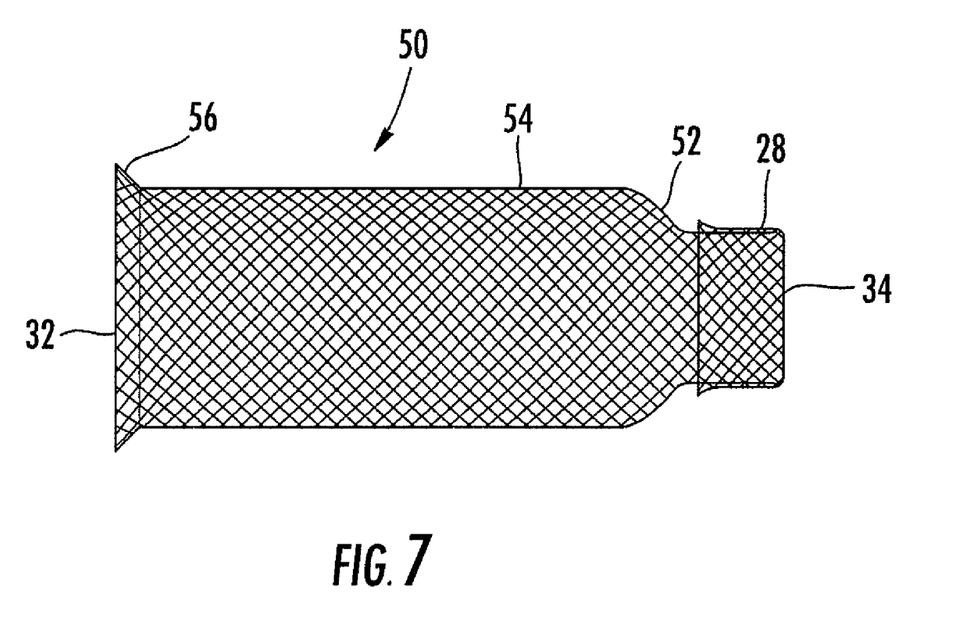
FIG. 7 is a side elevational view of a stent graft according to one embodiment of the present invention.

FIG. 7 illustrates an additional embodiment of the present invention. The stent graft 50 of FIG. 7 is "bullet" shaped and includes a folded portion 28 at its distal end 34 that is configured to be sized to engage the lumen 12. The stent graft 50 includes a tapered portion 52 that extends between a cylindrical portion 54 and the folded portion 28. In addition, the stent graft 50 includes a flared portion 56 at its proximal end 32 that is configured to anchor the stent graft in the lumen 12. Thus, the stent graft 50 is configured to substantially conform to an aneurysm 14, such as an early stage aneurysm that has not expanded significantly in diameter.

Various techniques could be employed to fabricate the stent graft 10. According to one embodiment, the inner 23 and outer 26 tubular structures are braided to form a tubular fabric made of an elastic metallic material such as Nitinol. The outer braided tubular structure 26 would then be concentrically disposed over the inner tubular structure 23, and the combination would be placed about a cylindrical mandrel of the desired outer diameter for the stent graft 10. One or more portions of the tubular structure 23 (e.g., the distal end 34) would be folded over upon itself to form one or more respective folded portions 28. This assembly would then be heated in a mold to a predetermined temperature and for a length of time sufficient to heat set the tubular structures to the diameter of the mandrel. Following removal from the mold, the two or more coaxial braided tubular structures 23, 26 may be held together by one or more connecting members, e.g., a radiopaque platinum wires or suture stitches. It is also contemplated that the stent graft 10 may be coated with a drug-eluting polymer for promoting or inhibiting thrombus formation, promoting tissue in growth into the stent graft or promotion of endothelial cells onto the stent graft or other desired effects. The drug-eluting polymer may be selectively coated on the open weave or closed weave segments. For further details regarding exemplary techniques for fabricating a stent graft 10, Applicants hereby incorporate by reference the contents of U.S. Pat. No. 6,123,715, filed Jul. 8, 1994, herein in its entirety.

In use, the stent graft 10 would be deployed within the lumen in a compressed or constrained diameter that is smaller than its heat set diameter. Typically, the stent graft 10 would be radially compressed or otherwise constrained to a smaller diameter and positioned within a delivery catheter 38 for delivery within the lumen. For instance, the stent graft 10 may be constrained to a diameter of about 6-15 French. In addition, the ratio of the diameter of the expanded heat set configuration to the diameter of the constrained configuration may vary from, for example, about 3:1 to 7:1.

Furthermore, the stent graft 10 may be releasably affixed at its proximal end 32 to a pusher catheter 40 via a clamp member 42. The stent graft 10 would then be drawn into a lumen of an intravascular delivery catheter 38. The delivery catheter 38 would be introduced into the patient, such as by using the Seldinger technique, and then guided through the vascular system until a distal end of the delivery catheter is proximate to an aneurysm 14 to be treated. With the stent graft 10 and the pusher catheter 40 held stationary, the delivery catheter 38 is withdrawn in the proximal direction to eject the stent graft from the distal end of the delivery catheter where the distal end 34 of the stent graft then self-expands to engage the lumen 12 with a portion of stent graft bridging the aneurysm 14 being treated. The ends of the braided wire strands at the distal end 34 of the stent graft dig into the walls, or otherwise engage, the lumen 12 (e.g., the folded portion may radially engage the lumen in the configuration shown in FIG. 3). The physician may then move the push catheter 40 slightly distally so as to begin to fold the distal end over on itself (e.g., the folded portion would resemble FIG. 4 at this stage). The delivery catheter 38 is then withdrawn proximally while holding the pusher catheter 40 stationary such that the fold back portion continues to fold over on itself to form the folded portion 28 (e.g., the folded portion may fold back on itself as shown in FIGS. 5 and 6). When the stent graft 10 is fully deployed from the delivery catheter 38, the clamp member 42 is actuated so as to release the proximal end and allow the proximal end to self expand to contact the lumen 12. As shown in FIG. 1, the stent graft 10 may be positioned such that the stent graft bridges an aneurysm, with the folded portion 28 engaging the lumen 12 upstream of the aneurysm and the proximal end of the stent graft engaging the lumen 12 downstream of the aneurysm. For further exemplary details regarding a delivery catheter, a pusher catheter, clamp member, and methods of using the same, Applicants hereby incorporate U.S. Patent Appl. Publ. No. 2006/0253184, filed May 4, 2005, herein in its entirety.

Embodiments of the present invention may provide several advantages. For example, the folded portion 28 of the stent graft 10 may provide additional fixation within the lumen 12 to reduce the incidence of migration. In this regard, the ends of the folded portion 28 may include ends of individual strands of braided material that dig into the lumen 12 prior to being folded over on itself or the ends may be heat set at an angle to the vessel wall to engage the wall. The folded portion 28 may also provide an increased diameter at the proximal 32 and/or distal 34 ends of the stent graft 10 that may anchor the stent graft within the lumen 12. In addition, the folded portion 28 may provide additional hoop strength around the circumference of the stent graft so as to resist radial forces on the lumen 12, such as pressure from blood flowing through the stent graft 10.

One embodiment provides a stent graft 10 that includes an occluding material that may be used to prophylactically treat an aneurysm before becoming large enough to pose a health risk to the patient. In particular, because the stent graft 10 may be constrained to be deployed within a delivery catheter 38 having a smaller inner diameter (e.g., less than 15 French), the stent graft may be more easily delivered within smaller vessels and veins so as to proactively treat aneurysms or other vascular abnormalities before they pose a significant health risk. The occluding material also facilitates occlusion of the lumen 12 proximate to a vascular abnormality such that additional thrombogenic techniques may be unnecessary.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A stent graft for treating a vascular abnormality in a lumen, the stent comprising:
a flexible tubular structure comprising a proximal end and a distal end and having an expanded heat set configuration, wherein the tubular structure is configured to be constrained to a smaller diameter than the expanded heat set configuration, and wherein the tubular structure is heat set such that at least a portion of the proximal and/or distal ends is inverted against, and in direct contact with, itself when unconstrained.

2. The stent graft of claim 1, wherein the tubular structure comprises a plurality of layers of braided strands.

3. The stent graft of claim 2, wherein the plurality of layers comprise respective tubular structures coaxially disposed in an overlying relationship and that are joined together by a connecting member.

4. The stent graft of claim 1, wherein the tubular structure comprises braided strands of an elastic metallic alloy.

5. The stent graft of claim 1, wherein the tubular structure comprises an inner surface and an outer surface, and wherein the tubular structure is inverted against itself when unconstrained such that at least a portion of the inner surface of the tubular structure at the proximal and/or distal ends is facing outwardly to engage the lumen.

6. The stent graft of claim 5, wherein the tubular structure is folded back against itself when unconstrained such that a first portion of the outer surface lies adjacent to, and in direct contact with, a second portion of the outer surface.

7. The stent graft of claim 1, wherein the tubular structure is inverted within itself when unconstrained such that at least a portion of the outer surface of the tubular structure at the proximal end is facing inwardly.

8. The stent graft of claim 1, wherein the tubular structure is inverted against itself about a circumference of the tubular structure when unconstrained.

9. The stent graft of claim 1, wherein the tubular structure is configured to be constrained to a diameter of less than about 15 French for delivery within a catheter.

10. The stent graft of claim 1, wherein the tubular structure is configured to be constrained to a diameter of less than about 12 French for delivery within a catheter.

11. The stent graft of claim 1, wherein the tubular structure is configured to be constrained to a diameter of less than about 10 French for delivery within a catheter.

12. The stent graft of claim 1, wherein the tubular structure is configured to be constrained to a diameter of less than about 8 French for delivery within a catheter.

13. The stent graft of claim 1, wherein the tubular structure is configured to engage the lumen upstream and downstream of an aneurysm.

14. The stent graft of claim 1, wherein the tubular structure is inverted against itself without applying a compressive force thereto or employing a weakened fold line.

15. The stent graft of claim 1, wherein a ratio of a diameter of the expanded heat set configuration to the smaller second diameter is within the range of about 3:1 to 7:1.

16. The stent graft of claim 1, wherein the tubular structure is configured to be elongated from the expanded heat set configuration to a smaller diameter whereby the tubular structure is unfolded prior to deploying the tubular structure.

17. The stent graft of claim 1, wherein the proximal and/or distal end of the tubular structure is folded back against itself when unconstrained such that a first portion of the tubular structure at the proximal and/or distal end lies adjacent to, and in direct contact with, a second portion of the tubular structure along an entire length thereof.

18. A method for treating a vascular abnormality in a lumen, the method comprising:
constraining a stent graft to a smaller diameter than an expanded heat set configuration;
delivering the stent graft proximate to the vascular abnormality in the lumen; and
deploying the stent graft such that at least a portion of the proximal and/or distal ends self expands from the constrained smaller diameter and returns to its expanded heat set configuration, inverts over against, and in direct contact with, itself, and engages the lumen.

19. The method of claim 18, wherein deploying comprises deploying the stent graft such that the stent graft engages the lumen upstream and downstream of an aneurysm.

20. The method of claim 18, wherein deploying comprises urging the stent graft distally after the distal end initially expands outwardly to engage the lumen.

21. The method of claim 20, wherein deploying comprises further deploying the stent graft after the distal end is urged distally such that the distal end inverts against itself.

22. The method of claim 18, wherein deploying comprises deploying the stent graft such that at least a portion of an inner surface of the stent graft at the distal end inverts to face outwardly to engage the lumen.

23. The method of claim 18, wherein deploying comprises deploying the stent graft such that at least a portion of the stent inverts against itself about a circumference thereof.

24. The method of claim 18, wherein constraining comprises radially compressing the stent graft to a diameter of less than about 15 French.

25. The method of claim 18, wherein constraining comprises elongating the stent graft to a smaller diameter whereby the stent graft is unfolded prior to the deploying step.

26. The method of claim 18, wherein delivering comprises delivering the stent graft over a guide wire.

27. A stent graft for treating a vascular abnormality in a lumen, the stent graft comprising:
a tubular structure comprising an occlusive material and having a proximal end and a distal end, wherein the tubular structure has an expanded heat set configuration and is configured to be elongated to a smaller diameter than the expanded heat set configuration whereby the tubular structure is unfolded prior to being deployed, and wherein the tubular structure is heat set such that at least a portion of the tubular structure is folded over against, and in direct contact with, itself when deployed.

28. The stent graft of claim 27, wherein the tubular structure is heat set such that at least a portion of the proximal and/or distal ends is inverted against itself when deployed.

29. The stent graft of claim 28, wherein the tubular structure comprises an inner surface and an outer surface, and wherein the tubular structure is inverted against itself when deployed such that at least a portion of the inner surface of the tubular structure at the proximal and/or distal ends is facing outwardly to engage the lumen.

30. The stent graft of claim 27, wherein the occlusive material comprises braided strands.

31. A stent graft for treating a vascular abnormality in a lumen, the stent comprising:
a flexible tubular structure having an expanded heat set configuration including one or more folded portions, wherein the tubular structure is configured to be constrained to a smaller diameter than the expanded heat set configuration whereby the tubular structure is unfolded prior to being deployed, and wherein the tubular structure is heat set such that at least a portion of the tubular structure is folded over against, and in direct contact with, itself when unconstrained.

* * * * *